US012767686B2

(12) United States Patent
Upadhyay et al.

(10) Patent No.: US 12,767,686 B2
(45) Date of Patent: Oct. 20, 2026

(54) SEPARATION OF PRE-PEAK AND POST-PEAK IN FUSION PROTEIN SAMPLE BY USING SIZE EXCLUSION HIGH PERFORMANCE LIQUID CHROMATOGRAPHY

(71) Applicant: Kashiv BioSciences, LLC, Piscataway, NJ (US)

(72) Inventors: Roshan Ganeshlal Upadhyay, Ahmedabad (IN); Darshana Jiten Maniar, Ahmedabad (IN); Shivani Singh, Ahmedabad (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 0 days.

(21) Appl. No.: 18/629,465

(22) Filed: Apr. 8, 2024

(65) Prior Publication Data

US 2024/0254160 A1 Aug. 1, 2024

Related U.S. Application Data

(63) Continuation of application No. PCT/IB2022/059649, filed on Oct. 8, 2022.

(30) Foreign Application Priority Data

Oct. 8, 2021 (IN) ............................. 202121045959

(51) Int. Cl.

*A61K 39/395* (2006.01)
*B01D 15/34* (2006.01)
*B01J 20/28* (2006.01)
*B01J 20/283* (2006.01)
*C07K 1/16* (2006.01)
*C07K 14/705* (2006.01)

(52) U.S. Cl.

CPC ................ *C07K 1/16* (2013.01); *B01D 15/34* (2013.01); *B01J 20/28083* (2013.01); *B01J 20/283* (2013.01); *C07K 14/70521* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 5,328,834 | A | 7/1994 | Ngo et al. |
| 8,703,126 | B2 | 4/2014 | Liu et al. |
| 9,291,630 | B1 | 3/2016 | Wezeman et al. |
| 9,352,035 | B2 | 5/2016 | Zhou et al. |
| 9,382,317 | B2 | 7/2016 | Manning et al. |
| 9,556,258 | B2 | 1/2017 | Nti-Gyabaah et al. |
| 9,598,718 | B2 | 3/2017 | Rupprechter et al. |
| 9,683,012 | B2 | 6/2017 | Yoon et al. |
| 10,034,940 | B2 | 7/2018 | Liu et al. |
| 10,080,793 | B2 | 9/2018 | van't Oever et al. |
| 10,618,960 | B2 | 4/2020 | Liu et al. |
| 12,139,510 | B2 | 11/2024 | Narayan et al. |
| 2006/0228780 | A1 | 10/2006 | Luo et al. |
| 2008/0064861 | A1 | 3/2008 | Sun |
| 2008/0167450 | A1 | 7/2008 | Pan |
| 2009/0252749 | A1 | 10/2009 | Leister et al. |
| 2010/0129379 | A1 | 5/2010 | Carpenter et al. |
| 2010/0278929 | A1 | 11/2010 | Wei et al. |
| 2011/0129468 | A1 | 6/2011 | Mccue et al. |
| 2012/0172299 | A1 | 7/2012 | Schmalz et al. |
| 2012/0322733 | A1 | 12/2012 | Shaw |
| 2013/0079498 | A1 | 3/2013 | Gilljam et al. |
| 2013/0197198 | A1 | 8/2013 | Sun et al. |
| 2013/0338344 | A1 | 12/2013 | Ramasubramanyan et al. |
| 2014/0288272 | A1 | 9/2014 | Allison et al. |
| 2014/0341843 | A1 | 11/2014 | Barnes et al. |
| 2015/0284673 | A1 | 10/2015 | Langer et al. |
| 2016/0115193 | A1 | 4/2016 | Herigstad et al. |
| 2016/0122384 | A1 | 5/2016 | Kim et al. |
| 2016/0228371 | A1 | 8/2016 | Schultz et al. |
| 2017/0007712 | A1 | 1/2017 | DeFrees et al. |
| 2017/0058019 | A1 | 3/2017 | Felföldi et al. |
| 2017/0305999 | A1 | 10/2017 | Leber et al. |
| 2017/0326069 | A1 | 11/2017 | Brunner-Schwarz et al. |
| 2018/0037642 | A1 | 2/2018 | Arakawa et al. |
| 2018/0208639 | A1 | 7/2018 | Minter et al. |

(Continued)

FOREIGN PATENT DOCUMENTS

| | | | |
|---|---|---|---|
| CA | 2528906 | C | 7/2013 |
| CA | 3072129 | A1 | 3/2019 |

(Continued)

OTHER PUBLICATIONS

Yang et al, J. of Pharmaceutical and biomedical analysis, vol. 109, p. 52-61 (Year: 2015).*
Ahmed et al. J of Chromatography, vol. 599, p. 25-33 (Year: 1992).*
U.S. Appl. No. 17/922,729 20230167153, filed Nov. 1, 2022.
U.S. Appl. No. 18/416,846 20240158437, filed Jan. 18, 2024.
U.S. Appl. No. 18/416,844 20240239838, filed Jan. 18, 2024.
U.S. Appl. No. 17/922,734 20230166200, filed Nov. 1, 2022.
U.S. Appl. No. 17/922,742 20230166201, filed Nov. 1, 2022.
U.S. Appl. No. 17/928,101 20230348530, filed Nov. 28, 2022.
U.S. Appl. No. 17/627,477 2022-0260521, filed Jan. 14, 2022.
U.S. Appl. No. 17/682,314 2022-0267473, filed Feb. 28, 2022.

(Continued)

*Primary Examiner* — Yunsoo Kim
(74) *Attorney, Agent, or Firm* — Goodwin Procter LLP

(57) ABSTRACT

The present invention provides an effective High Performance Liquid Chromatography (SE-HPLC) method to separate or resolve the pre-peak, post-peak and main peak of CTLA4-IgG1 fusion protein, where pre-peak resolution is more than 1.3. The invention further provides effective separation and resolution of post peak impurity present in CTLA4 IgG1 protein. Moreover, the present invention also provides the method for the estimation and/or quantification of pre-peak, post-peak and main peak of the protein mixture.

17 Claims, 6 Drawing Sheets

(56) References Cited

U.S. PATENT DOCUMENTS

| | | | |
|---|---|---|---|
| 2018/0327446 A1 | 11/2018 | Fong et al. |
| 2018/0344630 A1 | 12/2018 | Igawa et al. |
| 2019/0062419 A1 | 2/2019 | Ramasubramanyan et al. |
| 2019/0256556 A1 | 8/2019 | Giese et al. |
| 2019/0298801 A1 | 10/2019 | Kerwin et al. |
| 2019/0343918 A1 | 11/2019 | Graham et al. |
| 2019/0353661 A1 | 11/2019 | Smith |
| 2019/0358323 A1 | 11/2019 | Liu et al. |
| 2020/0003714 A1 | 1/2020 | Gillespie et al. |
| 2020/0017569 A9 | 1/2020 | Leister et al. |
| 2020/0088749 A1 | 3/2020 | Salbato et al. |
| 2020/0230242 A1 | 7/2020 | Desai et al. |
| 2020/0283472 A1 | 9/2020 | Karur |
| 2021/0079422 A1 | 3/2021 | Oh et al. |
| 2021/0122782 A1 | 4/2021 | Eisenhuth et al. |
| 2021/0130396 A1 | 5/2021 | Sutter et al. |
| 2021/0179690 A1 | 6/2021 | Jayaraman et al. |
| 2021/0230250 A1 | 7/2021 | Lazar et al. |
| 2022/0194980 A1 | 6/2022 | Leiss et al. |
| 2022/0203347 A1 | 6/2022 | Wong et al. |
| 2022/0260521 A1 | 8/2022 | Upadhyay |
| 2022/0267473 A1 | 8/2022 | Weaver et al. |
| 2023/0124565 A1 | 4/2023 | Yang et al. |
| 2023/0166200 A1 | 6/2023 | Narayan et al. |
| 2023/0166201 A1 | 6/2023 | Narayan et al. |
| 2023/0167153 A1 | 6/2023 | Narayan et al. |
| 2023/0303621 A1 | 9/2023 | Mahajan |
| 2023/0340080 A1 | 10/2023 | Sharma et al. |
| 2023/0348530 A1 | 11/2023 | Narayan et al. |
| 2024/0077483 A1 | 3/2024 | Kuppili et al. |
| 2024/0156907 A1 | 5/2024 | Narayan et al. |
| 2024/0158437 A1 | 5/2024 | Narayan et al. |
| 2024/0254160 A1 | 8/2024 | Upadhyay et al. |
| 2024/0287159 A1 | 8/2024 | Sharma et al. |
| 2024/0317799 A1 | 9/2024 | Narayan et al. |
| 2024/0343758 A1 | 10/2024 | Narayan et al. |
| 2024/0343776 A1 | 10/2024 | Narayan et al. |
| 2024/0400612 A1 | 12/2024 | Narayan et al. |
| 2025/0011395 A1 | 1/2025 | Narayan et al. |
| 2025/0043027 A1 | 2/2025 | Weaver et al. |
| 2025/0059230 A1 | 2/2025 | Upadhyay et al. |

FOREIGN PATENT DOCUMENTS

| | | | |
|---|---|---|---|
| WO | WO-1998/001549 | A2 | 1/1998 |
| WO | WO-2002/082066 | A1 | 10/2002 |
| WO | WO-2005/044856 | A2 | 5/2005 |
| WO | WO-2009/058769 | A1 | 5/2009 |
| WO | WO-2010/102241 | A1 | 9/2010 |
| WO | WO-2011/150110 | A1 | 12/2011 |
| WO | WO-2012/160032 | A1 | 11/2012 |
| WO | WO-2013/071396 | A1 | 5/2013 |
| WO | WO-2013/096791 | A1 | 6/2013 |
| WO | WO-2013/180647 | A1 | 12/2013 |
| WO | WO-2015/189832 | A1 | 12/2015 |
| WO | WO-2016/009049 | A1 | 1/2016 |
| WO | WO-2017/180594 | A1 | 10/2017 |
| WO | WO-2019/043067 | A1 | 3/2019 |
| WO | WO-2019/224842 | A1 | 11/2019 |
| WO | WO-2019/224843 | A1 | 11/2019 |
| WO | WO-2021/009669 | A2 | 1/2021 |
| WO | WO-2021/038532 | A1 | 3/2021 |
| WO | WO-2021/181417 | A1 | 9/2021 |
| WO | WO-2021/220251 | A1 | 11/2021 |
| WO | WO-2021/220252 | A1 | 11/2021 |
| WO | WO-2021/220253 | A1 | 11/2021 |
| WO | WO-2021/240458 | A2 | 12/2021 |
| WO | WO-2022/195505 | A1 | 9/2022 |
| WO | WO-2022/201056 | A1 | 9/2022 |
| WO | WO-2023/047368 | A1 | 3/2023 |
| WO | WO-2023/053030 | A1 | 4/2023 |
| WO | WO-2023/053031 | A1 | 4/2023 |
| WO | WO-2023/053032 | A1 | 4/2023 |
| WO | WO-2023/057994 | A1 | 4/2023 |
| WO | WO-2023/057995 | A1 | 4/2023 |
| WO | WO-2023/112000 | A2 | 6/2023 |
| WO | WO-2023/180977 | A1 | 9/2023 |

OTHER PUBLICATIONS

U.S. Appl. No. 17/934,950 20230340080, filed Sep. 23, 2022.
U.S. Appl. No. 18/657,920, filed May 8, 2024.
U.S. Appl. No. 18/125,616 20230303621, filed Mar. 23, 2023.
U.S. Appl. No. 18/262,316 20240077483, filed Jul. 20, 2023.
U.S. Appl. No. 18/550,920 20240156907, filed Sep. 15, 2023.
U.S. Appl. No. 18/620,649, filed Mar. 28, 2024.
U.S. Appl. No. 18/620,441, filed Mar. 28, 2024.
U.S. Appl. No. 18/620,255, filed Mar. 28, 2024.
U.S. Appl. No. 18/696,701, filed Mar. 28, 2024.
U.S. Appl. No. 18/699,511, filed Apr. 8, 2024.
U.S. Appl. No. 18/629,465, filed Apr. 8, 2024.
International Search Report and Written Opinion for PCT/IB2021/053658 mailed Sep. 14, 2021 (15 pages).
Guo et al. (2019) "Exploring metabolic biomarkers and regulation pathways of acute pancreatitis using ultra-performance liquid chromatography combined with a mass spectrometry-based metabolomics strategy," RSC Adv 9:12162-12173.
Goke, et al. (1988) "Identification of Rat Pancreatic Secretory Proteins after Separation by High-Performance Liquid Chromatography," Pancreas 3(2):199-206.
Martias, et al. (2021) "Optimization of Sample Preparation for Metabolomics Exploration of Urine, Feces, Blood and Saliva in Humans Using Combined NMR and UHPLC-HRMS Platforms," Molecules 26(4111) 16 pages.
Padfield, et al. (1986) "Separation of Guinea-Pig Pancreatic Juice Proteins by Reversed-Phase High-Performance Liquid Chromatography," Journal of Chroma. 369:133-141.
International Search Report and Written Opinion for PCT/IB2022/059058 mailed Feb. 16, 2023 (8 pages).
International Search Report and Written Opinion for PCT/IB2023/052862 mailed Jul. 27, 2023 (8 pages).
Friess et al., "Microarray-based identification of differentially expressed growth- and metastasis-associated genes in pancreatic cancer", Cellular and Molecular Life Sciences, vol. 60, Jun. 2003, pp. 1180-1199.
Herniman et al., "Development of ultrahigh-performance liquid chromatography/mass spectrometry and ultrahigh-performance supercritical fluid chromatography/mass spectrometry assays to determine the concentration of BitrexTM and sodium saccharin in homemade facemask fit testing solutions", Rapid Communications in Mass Spectrometry, vol. 34, Iss. 16, Jun. 3, 2020, pp. 1-6.
International Search Report and Written Opinion for PCT/IB2020/058080 mailed Feb. 8, 2021 (12 pages).
Turner et al., "Development of orthogonoal NISTmAb size heterogeneity control methods", Analytical and Bioanalytical Chemistry, Mar. 2018, vol. 410, No. 8, pp. 2095-2110. (16 pages).
Sobczak et al., "RNA structure analysis assisted by capillary electrophoresis", Nucleic Acids Research, Nov. 15, 2002, vol. 30, No. 22, e124. (8 pages).
International Search Report and Written Opinion for PCT/IB2020/056593 mailed Feb. 8, 2021 (10 pages).
Balbino et al., "The anti-IgE mAb omalizumab induces adverse reactions by engaging Fc receptors", J. Clin. Invest., 2020, 130(3):1330-1335.
International Search Report and Written Opinion for PCT/IB2021/054693 mailed Nov. 17, 2021 (7 pages).
Lou et al., "Liquid-liquid phase separation causes high turbidity and pressure during low pH elution process in Protein A chromatography", Journal of Chromatography, Jan. 28, 2017, vol. 1488, pp. 57-67. (11 pages).
Cohen et al., "Switching Reference Medicines to Biosimilars: A Systematic Literature Review of Clinical Outcomes", Drugs, Mar. 3, 2018, vol. 78, Iss. 4, pp. 463-478. (16 pages).
International Search Report and Written Opinion for PCT/IB2021/053660 mailed Aug. 12, 2021 (10 pages).

(56) References Cited

OTHER PUBLICATIONS

Singla et al., "Aggregation Kinetics for IgG1-Based Monoclonal Antibody Therapeutics", AAPS J., May 2016, 18(3):689-702. doi: 10.1208/s12248-016-9887-0. (14 pages).
Khawli et al., "Charge variants in IgG1: Isolation, characterization, in vitro binding properties and pharmacokinetics in rats", Mabs, Nov.-Dec. 2010, 2(6):613-24. doi: 10.4161/mabs.2.6.13333. (12 pages).
International Search Report and Written Opinion for PCT/IB2021/053659 mailed Jul. 22, 2021 (9 pages).
International Search Report and Written Opinion for PCT/IB2022/052651 mailed Jul. 1, 2022 (11 pages).
International Search Report and Written Opinion for PCT/IB2022/052377 mailed Jun. 30, 2022 (8 pages).
International Search Report and Written Opinion for PCT/IB2022/059238 mailed Feb. 24, 2023 (12 pages).
International Search Report and Written Opinion for PCT/IB2022/059239 mailed Feb. 14, 2023 (7 pages).
International Search Report and Written Opinion for PCT/IB2022/059240 mailed Feb. 23, 2023 (13 pages).
Shekhawat et al., "Structural similarity, characterization of Poly Ethylene Glycol linkage and identification of product related variants in biosimilar pegfilgrastim", 1-33, PLOS ONE Web. Mar. 13, 2019. (33 pages).
Aasim et al., "The role of ligands on protein retention in adsorption chromatography: A surface energetics approach", p. 618-624, Journal of Separation Science, vol. 37, Issue 6. Jan. 21, 2014.
Jing et al., "Separation of monocloncal antibody charge variants using cation exchange chromatography: Resins and separation conditions optimization", Separation and Purification Technology, vol. 235, Mar. 18, 2020.
R&D Systems, Inc., "Recombinant Human CTLA 4 Fc Chimera | Catalog No. 7268-CT". Product datasheet (online). Mar. 6, 2020. (2 pages).
International Search Report and Written Opinion for PCT/IB2022/059648 mailed Feburary 21, 2023 (8 pages).
International Search Report and Written Opinion for PCT/IB2022/059649 mailed Feburary 7, 2023 (8 pages).
International Search Report and Written Opinion for PCT/IB2022/062426 mailed Jun. 6, 2023 (8 pages).
Geng et al., "Inhibition of autoregulated TGFbeta signaling simultaneously enhances proliferation and differentiation of kidney epithelium and promotes repair following renal ischemia", Am. J. Pathol., Dec. 16, 2010, vol. 174, No. 4, pp. 1291-1308.
Molecular Probes, Protein Molecular Weight Standards (P-6649), Jan. 13, 2001, pp. 1-2.
Center for Drug Evaluation and Research et al., Product Quality Reviews 2024, FDA, pp. 1-161, https://www.accessdata.fda.gov/drugsatfda_docs/nda/2018/761075Orig 1 s000Chem R. pdf (Year: 2024).
GE Healthcare Life Sciences (2013) Multi modal Chromatography Handbook. GE Healthcare Bio-Sciences AB, Bjorkgatan 30, 751 84 Uppsala, Sweden, 2013, pp. 1-113.
Gu et al. (2019) "Assessment of CE-based baseline disturbances using simulation and targeted experimental evaluation-impact on the purity determination of therapeutic proteins," Analytical and Bioanalytical Chemistry 411:2425-2437.
Guttman et al. (2020) "Better Separation Resolution of New Biopharmaceutical Modalities through Fine Tuning of the Temperature with CE-SOS" SCIEX, pp. 1-5.
Lacher et al. (2010) "Development, validation, and implementation of capillary gel electrophoresis as a replacement for SDSPAGE for purity analysis of IgG2," mAbs, J. Sep. Sci. 33:218-227.
Lee et al. (2010) "Capillary Electrophoretic Separation of Poly(ethylene glycol)-Modified Granulocyte-Colony Stimulating Factor," Arch Pharm Res 22(3)491-495.
Liu et al. (2005) "Highly efficient approach for characterizing nanometer-sized gold particles by capillary electrophoresis," Analytica Chimica Acta 528: 249-254.
Lui et al. "(2010) Recovery and purification process development for monoclonal antibody production," mAbs 2(5):480-499.
Phenomenex: "High Performance Size Exclusion for Biomolecules," Oct. 4, 2010 (Oct. 4, 2010), XP093277516, Retrieved from the Internet: URL:https://phenomenex.blob.core.windows.net/documents/7b9fe422-933e-48df-a189-373e2 ef59503.pdf.
Sanger-van de Griend et al. (2019) "CE-SOS method development, validation, and best practice—An overview," Electrophoresis 40:2361-2374.
Somerville et al. (1999) "Discrimination of granulocyte colony-stimulating factor isoforms by high-performance capillary electrophoresis," Journal of Chromatography B, 732:81-89.
Voitl et al. (2010) "Application of mixed mode resins for the purification of antibodies," Journal of Chromatography A 1217:5753-5760.
Degterev et al. (2011) "Improvement of the Degradation Profiling of Eculizumab and Omalizumab Monoclonal Antibodies by Liquid Chromatography-Mass Spectrometry," Journal of Analytical Chemistry 76(14):1596-1609.
Ichiuhara et al. (2018) "Integrated flow-through purification for therapeutic monoclonal antibodies processing," MABS 10(2):325-334.
Pennington et al. (2016) "Structural basis of omalizumab therapy and omalizumab-mediated IgE exchange," Nature Communications 7:11610:1-12.
Wang et al. Characterization and pre-clinical assessment of a proposed biosimilar to its originator Omalizumab, Eur. J. Pharm Sci 178(1):106292 (2022).
Weisbjerg et al. (2015) "Serial Coupling of Ion-Exchange and Size-Exclusion Chromatography to Determine Aggregation Levels in mAbs in The Presence of a Proteinaceous Excipient, Recombinant Human Serum Albumin," Journal of Pharmaceutical Sciences 104:548-556.
Xolai R® (omalizumab) product insert https://www.accessdata.fda.gov/drugsatfda_docs/label/2023/103976s5242lbl.pdf 2003.
Xolair® (omalizumab) injection for subcutaneous use [package insert]. Accessdata.fda.gov. 2021. https://www.accessdata.fda.gov/drugsatfda_docs/label/2021/103976s5238lbl.pdf (Year: 2021).

* cited by examiner

SEPARATION OF PRE-PEAK AND POST-PEAK IN FUSION PROTEIN SAMPLE BY USING SIZE EXCLUSION HIGH PERFORMANCE LIQUID CHROMATOGRAPHY

CROSS-REFERENCE TO RELATED APPLICATIONS

This application is a Continuation of International Application No. PCT/IB2022/059649, filed on Oct. 8, 2022, which claims the benefit of and priority to Indian Patent Application number 202121045959, filed on Oct. 8, 2021, each of which is incorporated by reference herein in its entirety.

FIELD OF THE INVENTION

The present invention provides an effective High Performance Liquid Chromatography (SE-HPLC) method to separate or resolve the pre-peak, post-peak and main peak of CTLA4-IgG1 fusion protein, where pre-peak resolution is more than 1.3. The invention further provides effective separation and resolution of post peak impurity present in CTLA4 IgG1 protein. Moreover, the present invention also provides the method for the estimation and/or quantification of pre-peak, post-peak and main peak of the protein mixture.

BACKGROUND OF THE INVENTION

In the production of biologics, it is very important to develop robust process to provide protein with high purity and less impurities especially high molecular weight impurities (HMWs) and low molecular weight impurities (LMWs). In order to establish a successful downstream process, it is very imperative to analyze the post-harvest protein mixture to evaluate or characterize the impurities such as HMWs and LMWs. Size exclusion High Performance Liquid Chromatography is a technique to estimate or quantify pre-peak and post-peak but resolving a pre-peak and post-peak from main peak is very challenging and it is observed that routine Size exclusion High Performance Liquid Chromatography does not provide sharp resolution of pre-peak, post-peak and main peak of complex proteins such as antibody or fusion proteins. In absence of obtaining a sharp resolution, it is very difficult for skilled person to quantify the presence of pre-peak and post-peak adequately and it further creates uncertainty about the impurities during down-stream purification (DSP) which makes the DSP process expensive, ineffective, and lengthy. Therefore, it is very important to have an effective, robust Size exclusion High Performance Liquid Chromatography process to separate, estimate or quantify impurities such as HMW and LMW.

The present invention solves the problem and provide effective, robust Size exclusion High Performance Liquid Chromatography process to separate, estimate and/or quantify impurities present in fusion protein mixture such as high molecular weight impurities (HMWs) and low molecular weight impurities (LMWs).

SUMMARY OF THE INVENTION

In an embodiment, the invention provides the process for performing Size exclusion High Performance Liquid Chromatography to estimate and/or quantify impurities such as HMWs and LMWs present in protein mixture.

In an embodiment the method for the separation of CTLA4-IgG1 fusion protein mixture comprising CTLA4-IgG1 fusion protein, pre-peak and post-peak impurity thereof, the process comprises;

a) loading the CTLA4-IgG1 fusion protein mixture onto Size exclusion High Performance Liquid Chromatography (SE-HPLC) column;
b) separating the protein mixture with suitable mobile phase comprising combination of salts at suitable pH more than pI of the fusion protein; wherein the mobile phase maintains flow rate more than 0.3 mL/min;
c) separating the pre-peak impurity and post-peak impurity from the CTLA4-IgG1 fusion protein of interest, wherein the separation has pre-peak resolution is more than 1.3.

In an embodiment, the present invention provides a method for the separation of CTLA4-IgG1 fusion protein mixture comprising CTLA4-IgG1 fusion protein, pre-peak and post-peak impurity thereof, the process comprising;

a) loading the CTLA4-IgG1 fusion protein mixture onto Size exclusion High Performance Liquid Chromatography (SE-HPLC) column;
b) separating the protein mixture with suitable mobile phase comprising combination of salts at suitable pH more than pI of the fusion protein; wherein the mobile phase maintains flow rate more than 0.3 mL/min;
c) separating the pre-peak impurity and post-peak impurity from fusion protein of interest, wherein the separation has pre-peak resolution is more than 1.3.

In an embodiment, the invention separates the pre-peak, post-peak and main peak of fusion protein at suitable flow rate above 0.3 ml/min.

In an embodiment, the invention separates the pre-peak, post-peak and main peak of fusion protein at suitable flow rate selected from 0.35 ml/min, 0.4 ml/min, about 0.45 ml/min, about 0.5 ml/min, about 0.55 ml/min, about 0.6 ml/min, about 0.65 ml/min about 0.7 ml/min, about 0.75 ml/min and about 0.8 ml/min.

In an embodiment, the SE-HPLC column has silica matrix and pore size is selected from about 14 nm or 140 Å to about 29 nm or 290 Å.

In an embodiment, the SE-HPLC column has silica matrix and pore size is 14.5 nm or 145 Å.

In an embodiment, the loading concentration of protein mixture is selected from about 0.5 mg/ml to about 1.4 mg/ml.

In an embodiment, the loading amount of protein mixture is selected from about 10 μg to about 100 μg.

In an embodiment, the protein mixture can be obtained selected from cell culture harvest, protein A eluate, mixed mode chromatography eluate, anion exchange chromatography eluate, cation exchange chromatography eluate or after any other purification steps.

In an embodiment, the protein mixture can be obtained from harvest, partially purified, substantially purified by any other purification methods.

In an embodiment, the protein mixture is obtained from affinity chromatography, preferably protein A chromatography.

In an embodiment, the SE-HPLC column comprising silica-based resin. In certain embodiment, the column pore size is more than 120 Å. In an embodiment, the column pore size is selected from 14.5 nm or 145 Å to 29 nm or 290 Å. In certain embodiment, the columns are selected from Biosep SEC s2000, Biosep SEC s3000, Biosep SEC s4000.

In an embodiment, the invention provides USP peak tailing is from about 0.7 to about 1.15.

In certain embodiment, the pre-peak and post-peaks are not merged or interfered with main peak.

In an embodiment, the suitable detection absorbance is selected from about 214 nm to about 280 nm. In an embodiment, the detection absorbance is 215 nm.

In an embodiment, the invention provides purity of fusion protein of interest or main peak more than 98%.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) column;
c) separating the protein mixture with suitable mobile phase comprising combination of salts at suitable pH;
d) analysed or quantified the pre-peak, post-peak and main peak of the protein mixture at suitable detection absorbance.

In an embodiment, the suitable pH of mobile phase is selected from about 5.5 to about 7.0.

In certain embodiment, the suitable pH of mobile phase is selected from about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0.

In an embodiment the method for the separation of CTLA4-IgG1 fusion protein mixture comprising CTLA4-IgG1 fusion protein, pre-peak and post-peak impurity thereof, the process comprises;

a) loading the CTLA4-IgG1 fusion protein mixture onto Size exclusion High Performance Liquid Chromatography (SE-HPLC) Biosep SEC s2000 column;
b) separating the protein mixture with suitable mobile phase comprising combination of salts at suitable pH; wherein the salts is selected from phosphate, sodium and sulphate salts. wherein the mobile phase maintains flow rate more than 0.3 mL/min.
c) separating the pre-peak impurity and post-peak impurity from the CTLA4-IgG1 fusion protein of interest, wherein the separation has pre-peak resolution is more than 1.3.
d) analysed or quantified the pre-peak, post-peak and main peak of the CTLA4-IgG1 fusion protein mixture.

In certain embodiment, the pre-peak area and post-peak is not merged or interfered with main peak area.

In an embodiment, the present invention provides an improved method for quantification and/or estimation of impurities in a protein sample comprising;

a) a protein mixture from harvest comprising protein of interest and size variants impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are Sodium phosphate in combination with Sodium sulphate in suitable concentration;
d) analysed or quantified the pre-peak, post-peak and main peak of the protein mixture; wherein the SE-HPLC column provides the resolution of pre-peak is more than 1.3.

In such embodiment, the concentration of mobile phase Sodium phosphate is selected from about 50 mM, about 60 mM, about 65 mM, about 70 mM, about 75 mM, about 80 mM, about 85 mM, about 90 mM, about 95 mM, about 100 mM, about 105 mM, about 110 mM, 115 mM, about 120 mM, about 125 mM, about 130 mM, about 135 mM, about 140 mM, about 145 mM, and about 150 mM.

In such embodiment, the concentration of mobile phase Sodium sulphate is selected from about 50 mM, about 60 mM, about 65 mM, about 70 mM, about 75 mM, about 80 mM, about 85 mM, about 90 mM, about 95 mM, about 100 mM, about 105 mM, about 110 mM, 115 mM, about 120 mM, about 125 mM, about 130 mM, about 135 mM, about 140 mM, about 145 mM, and about 150 mM.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are 100 mM Sodium phosphate in combination with 100 mM Sodium sulphate in suitable concentration;
d) analysed or quantified the pre-peak, post-peak and main peak of the protein mixture wherein the SE-HPLC column provides the resolution of pre-peak is more than 1.3.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are 100 mM Sodium phosphate in combination with 200 mM Sodium sulphate in suitable concentration;
d) analysed or quantified the pre-peak, post-peak and main peak of the protein mixture wherein the SE-HPLC column provides the resolution of pre-peak is more than 1.3.

In such embodiment, the concentration of mobile phase Sodium sulphate is selected from about 50 mM, about 60 mM, about 65 mM, about 70 mM, about 75 mM, about 80 mM, about 85 mM, about 90 mM, about 95 mM, about 100 mM, about 120 mM, about 130 mM, about 140 mM, about 150 mM, about 160 mM, about 170 mM, about 180 mM, about 190 mM, about 200 mM, about 210 mM, and about 220 mM.

In certain embodiment, the pH of mobile phase is selected from about 5.5, about 6.0, about 6.1, about 6.2, about 6.3, about 6.4, about 6.5, about 6.6, about 6.7, about 6.8, about 6.9, and about 7.0.

In an embodiment, the pH of mobile phase is 6.5.

In an embodiment, the present invention provides an improved method for quantification and/or estimation of impurities in a protein sample comprising;

a) a protein mixture from harvest comprising CTLA4-IgG1 and size variant impurities;
b) loading the protein mixture to said Size exclusion High Performance Liquid Chromatography (SE-HPLC) Biosep SEC s2000 column;

c) separating the protein mixture with suitable mobile phase comprising combination of 100 mM Sodium phosphate in combination with 100 mM Sodium sulphate at pH 6.5;

d) analysed or quantified the pre-peak, post-peak and main peak of the protein mixture wherein the SE-HPLC column provides the resolution of pre-peak is more than 1.3.

In an embodiment, the present invention provides an improved method for quantification and/or estimation of impurities in a protein sample comprising;

a) a protein mixture from harvest comprising CTLA4-IgG1 and size variant impurities;

b) loading the protein mixture to said Size exclusion High Performance Liquid Chromatography (SE-HPLC) Biosep SEC s2000 column;

c) separating the protein mixture with suitable mobile phase comprising combination of 100 mM Sodium phosphate in combination with 200 mM Sodium sulphate at pH 6.5 d) analysed or quantified the pre-peak, post-peak and main peak of the protein mixture; wherein the SE-HPLC column provides the resolution of pre-peak is more than 1.3.

In an embodiment, the resolution of pre-peak is from about 1.3 to about 1.9.

DETAIL DESCRIPTION OF THE INVENTION

Figure 1:
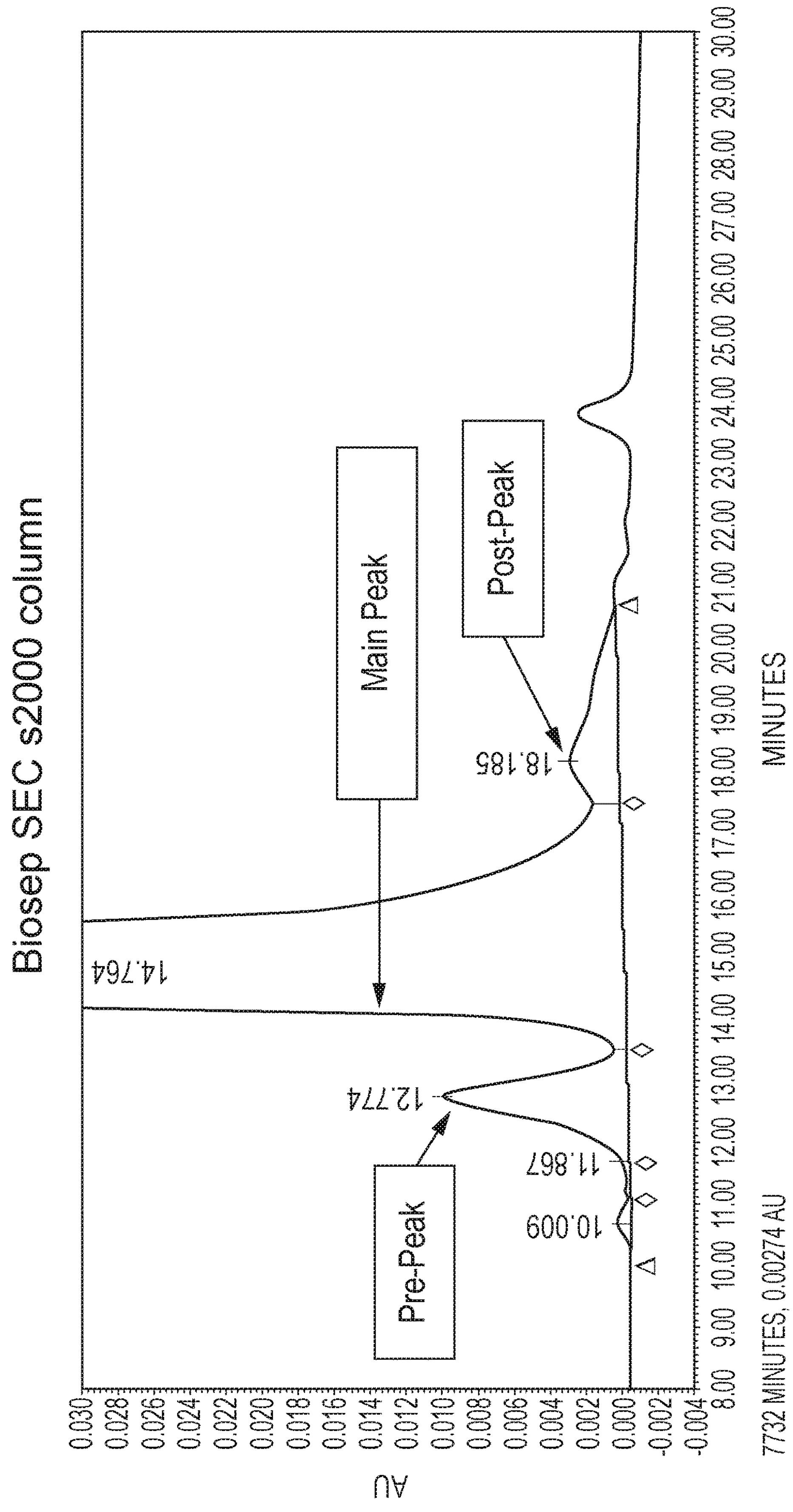
FIG. 1 shows separation of post-peak in Biosep SEC s2000 column.
Figure 2:
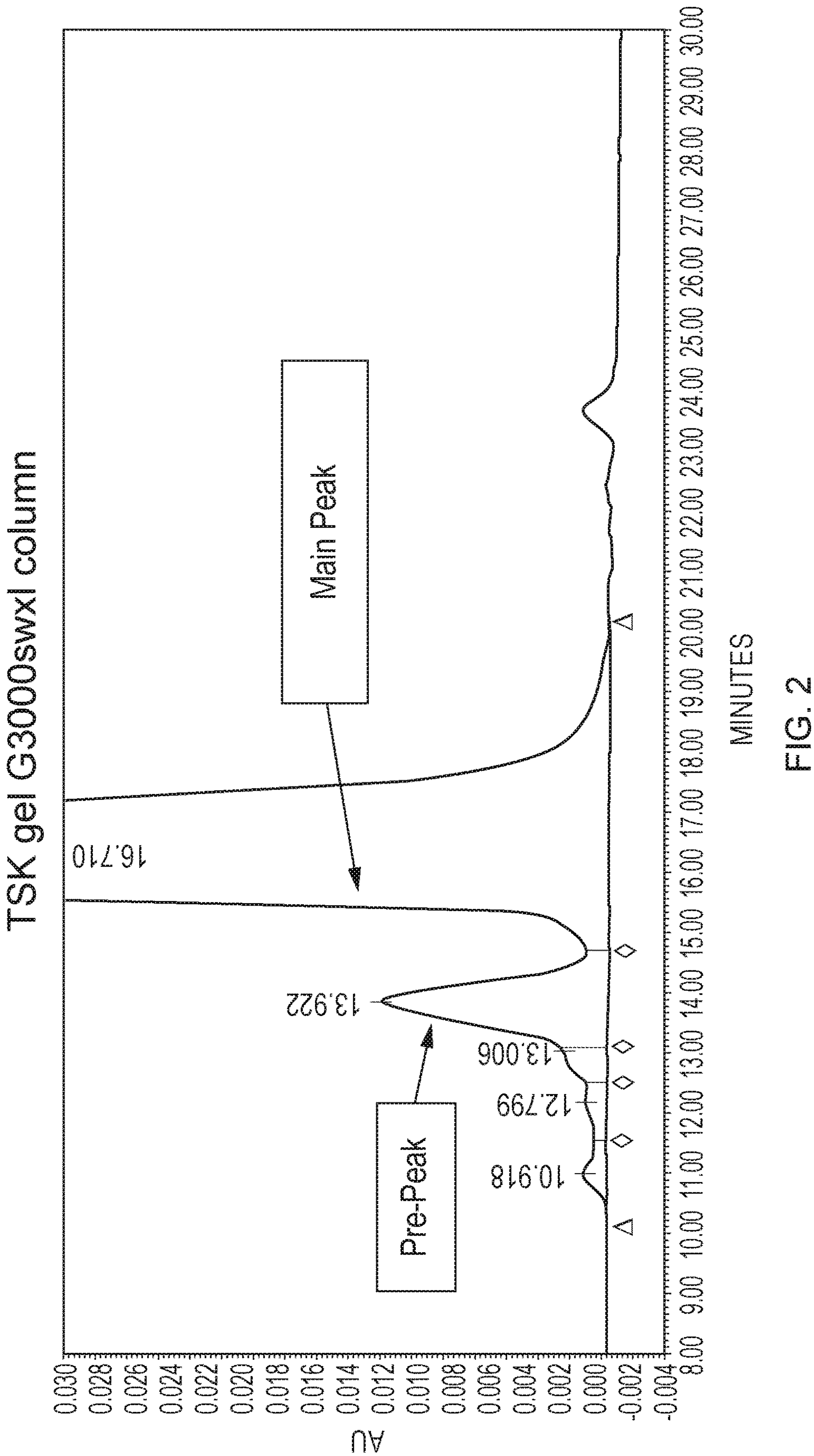
FIG. 2 shows no separation of post-peak in TSK gel G3000swxl column.

The present invention relates to an improved method for analysis of protein mixture comprises of at least one antibody or fusion protein, wherein the analysis of protein mixtures is performed with Size Exclusion High Performance Liquid Chromatography (SE-HPLC).

The term "Size Exclusion High Performance Liquid Chromatography (SE-HPLC)" refers to chromatography processes that employs porous particles in the column to separate molecules by virtue of their size in solution. SE-HPLC is generally used to separate biological molecules, to determine molecular weight distributions of proteins. Hence size variants of the protein CTAL4-IgG1 or CTLA4-IgG1 fusion protein can be separated by SE HPLC and purity of the main peak of CTLA4-IgG1 fusion protein can be determined. The separation can be achieved by using size exclusion column with isocratic elution using a mobile phase and detection by UV at 215 nm.

As used throughout the specification and in the appended claims, the singular forms "a", "an", and "the" include the plural reference unless the context clearly dictates otherwise.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "comprises" or "comprising" is used in the present description, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

The term "CTLA4-IgG1" or "CTLA4-IgG1 fusion protein" or "fusion protein of interest" or "fusion protein" used herein are interchangeable refers to a recombinant DNA generated fusion protein used to treat the symptoms of rheumatoid arthritis and to prevent joint damage caused by these conditions. CTLA4-IgG1 fusion protein is a biological product developed for immunosuppression by blocking T cell activation through inhibition of costimulatory signals and is indicated for treatment of rheumatoid arthritis. CTLA4-IgG1 fusion protein is a soluble homodimeric fusion protein of two identical subunits covalently linked by one disulfide bond. Each subunit consists of the modified amino acid sequence of the human cytotoxic lymphocyte associated antigen 4 (CTLA4), human immunoglobin IgG1 hinge, CH2 and CH3 region (Fc). Modification to the original sequences were introduced to avoid unintended disulfide bond formation and to reduce the ability of complement activation. Fusion protein examples such as TNF receptor 2-Fc (etanercept), rilonacept (Arcalyst—an IL-1 Trap), vascular endothelial growth factor trap (aflibercept), CTLA4-Fc fusion proteins (Abatacept and belatacept).

The term "protein mixture" and "protein sample" are interchangeable respectively in the present invention.

The term "Percentage (%) purity" refers to the percent of purity that determine the purity of protein present in the sample.

The term used "Percentage (%) purity" and "main peak area percentage (%)" are interchangeable respectively in the present invention.

The term "Percentage (%) molecular weight related impurities" refers to percent of high molecular weight impurities and low molecular weight impurities.

The term "pre peak area percentage (%)" refers to the percent of peak area that comes before the main peak area. The pre peak area includes high molecular weight aggregates.

The term "post peak area percentage (%)" refers to the percent of peak area that comes after the main peak area. The post peak area includes low molecular weight aggregates.

The term used "high molecular weight" or "HMW" is product-related impurities that contribute to the size heterogeneity of fusion protein drug product. The formation of HMW species within a therapeutic fusion protein drug product as a result of protein aggregation can potentially compromise both drug efficacy and safety (e.g., eliciting unwanted immunogenic response). HMW is considered critical quality attribute that are routinely monitored during drug development and as part of release testing of purified drug product during manufacturing. In certain embodiment the HMW relates to aggregates.

The term used "low molecular weight" or "LMW" species which is a protein backbone-truncated fragments & considered as product-related impurities that contribute to the size heterogeneity of fusion protein. LMW species often have low or substantially reduced activity relative to the monomeric form of the fusion protein and can lead to immunogenicity or potentially impact pharmacokinetic properties in vivo. As a result, LMW species are considered critical quality attributes that are routinely monitored during drug development and as part of release testing of purified drug product during manufacturing.

The term "column" refers to the column of SE-HPLC selected from bioZen SEC-2, bioZen SEC-3, MabPac SEC-1, BioBasic SEC 60, BioBasic SEC 120, YMC SEC Mab, YMC-Pack Diol-200, Biosep SEC s4000, Biosep SEC s3000 and Biosep SEC s2000.

In an embodiment, the column used for SE-HPLC selected from MabPac SEC-1, YMC SEC Mab, Biosep SEC s3000 and Biosep SEC s2000.

In preferred embodiment, the column used for SE-HPLC is Biosep SEC s2000.

The term "pI" or "Isoelectric point" used herein are interchangeable refers to the pH of a solution at which the net charge of a protein becomes zero. At solution pH that is above the pI, the surface of the protein is predominantly negatively charged, and therefore like-charged molecules will exhibit repulsive forces. Likewise, at a solution pH that is below the pI, the surface of the protein is predominantly positively charged, and repulsion between proteins occurs. The pI of CTLA4-IgG1 is less than 6.5.

The term "mobile phase" refers to mobile phase having salts selected from sodium phosphate, sodium sulphate, sodium chloride, potassium phosphate, potassium chloride, calcium chloride, and calcium phosphate.

The term "flow rate" refers to amount of mobile phase passing through the column in unit time.

In an embodiment, mobile phase having salts selected from sodium phosphate, sodium sulphate, potassium phosphate, and potassium chloride.

In other embodiment, the mobile phase having salts selected from sodium phosphate in combination with sodium sulphate, potassium phosphate in combination with potassium chloride, sodium phosphate in combination with potassium chloride, and potassium phosphate in combination with sodium sulphate.

In preferred embodiment, mobile phase having salts are sodium phosphate in combination with sodium sulphate.

In an embodiment, the present invention provides a process for the separation of protein mixture comprising fusion protein of interest, pre-peak impurity, and post-peak impurity, the process comprising;

a) loading the protein mixture onto Size exclusion High Performance Liquid Chromatography (SE-HPLC) column;
b) separating the protein mixture with suitable mobile phase comprising combination of salts at suitable pH more than pI of the fusion protein; wherein the mobile phase maintains flow rate more than 0.3 mL/min;
c) separating the pre-peak impurity and post-peak impurity from fusion protein of interest, wherein the separation has pre-peak resolution is more than 1.3.

In an embodiment, the invention separates the pre-peak, post-peak and main peak of fusion protein at suitable flow rate above 0.3 ml/min.

In an embodiment, the invention separates the pre-peak, post-peak and main peak of fusion protein at suitable flow rate selected from 0.35 ml/min, 0.4 ml/min, about 0.45 ml/min, about 0.5 ml/min, about 0.55 ml/min, about 0.6 ml/min, about 0.65 ml/min about 0.7 ml/min, about 0.75 ml/min and about 0.8 ml/min.

In an embodiment, the loading concentration of protein mixture is selected from about 0.5 mg/ml to about 1.4 mg/ml.

In an embodiment, the loading amount of protein mixture is selected from about 10 μg to about 100 μg.

In an embodiment, the loading of protein mixture comprises about 30 μg/μl to about 80 μg/μl.

In an embodiment, the loading of protein mixture is about 30 μg/μl.

In an embodiment, the protein mixture can be obtained selected from cell culture harvest, protein A eluate, mixed mode chromatography eluate, anion exchange chromatography eluate, cation exchange chromatography eluate or after any other purification steps.

In an embodiment, the SE-HPLC column comprising silica-based resin preferably diol type silica-based resin. In certain embodiment, the column pore size is more than 120 Å. In an embodiment, the column pore size is selected from 14.5 nm or 145 Å to 50 nm or 500 Å. In certain embodiment, the columns are selected from Biosep SEC s2000, Biosep SEC s3000, Biosep SEC s4000.

In an embodiment, the invention provides USP peak tailing is from about 0.7 to about 1.15.

In certain embodiment, the pre-peak and post-peaks are not merged or interfered with main peak.

In an embodiment, the suitable detection absorbance is selected from about 214 nm to about 280 nm. In an embodiment, the detection absorbance is 215 nm.

In an embodiment, the invention provides purity of fusion protein of interest or main peak more than 98%.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) column;
c) separating the protein mixture with suitable mobile phase comprising combination of salts at suitable pH;
d) analysed or quantified the pre-peak, post-peak and main peak of the protein mixture at suitable detection absorbance.

In an embodiment, the suitable pH of mobile phase is selected from about 5.5 to about 7.0.

In certain embodiment, the suitable pH of mobile phase is selected from about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts is selected from phosphate, sodium and sulphate salts;
d) analysed or quantified the pre-peak, post-peak and main peak of the protein mixture.

In certain embodiment, the pre-peak area and post-peak is not merged or interfered with main peak area.

In an embodiment, the present invention provides an improved method for quantification and/or estimation of impurities in a protein sample comprising;

a) a protein mixture from harvest comprising protein of interest and size variants impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are Sodium phosphate in combination with Sodium sulphate in suitable concentration;
d) analysed or quantified the pre-peak, post-peak and main peak of the protein mixture; wherein the SE-HPLC column provides the resolution of pre-peak is more than 1.3.

In such embodiment, the concentration of mobile phase Sodium phosphate is selected from about 60 mM, about 65 mM, about 70 mM, about 75 mM, about 80 mM, about 85 mM, about 90 mM, about 95 mM, about 100 mM, about 105 mM, about 110 mM, 115 mM, about 120 mM, about 125 mM, about 130 mM, about 135 mM, about 140 mM, about 145 mM, and about 150 mM.

In such embodiment, the concentration of mobile phase Sodium sulphate is selected from about 60 mM, about 65 mM, about 70 mM, about 75 mM, about 80 mM, about 85 mM, about 90 mM, about 95 mM, about 100 mM, about 105 mM, about 110 mM, 115 mM, about 120 mM, about 125 mM, about 130 mM, about 135 mM, about 140 mM, about 145 mM, and about 150 mM.

In an embodiment, the present invention provides an improved method for quantification and/or estimation of impurities in a protein sample comprising;

a) a protein mixture from harvest comprising protein of interest and size variant impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are 100 mM Sodium phosphate in combination with 100 mM Sodium sulphate in suitable concentration;
d) analysed or quantified the pre-peak, post-peak and main peak of the protein mixture; wherein the SE-HPLC column provides the resolution of pre-peak is more than 1.3.

In an embodiment, the present invention provides an improved method for quantification and/or estimation of impurities in a protein sample comprising;

a) a protein mixture from harvest comprising protein of interest and size variants impurities;
b) loading the protein mixture to said Size exclusion High Performance Liquid Chromatography (SE-HPLC) Biosep SEC s2000 column;
c) separating the protein mixture with suitable mobile phase comprising combination of salts at suitable pH; wherein the salts are 100 mM Sodium phosphate in combination with 200 mM Sodium sulphate in suitable concentration;
d) analysed or quantified the pre-peak, post-peak and main peak of the protein mixture; wherein the SE-HPLC column provides the resolution of pre-peak is more than 1.3.

In such embodiment, the concentration of mobile phase Sodium sulphate is selected from about 60 mM, about 65 mM, about 70 mM, about 75 mM, about 80 mM, about 85 mM, about 90 mM, about 95 mM, about 100 mM, about 120 mM, about 130 mM, about 140 mM, about 150 mM, about 160 mM, about 170 mM, about 180 mM, about 190 mM, about 200 mM, about 210 mM, and about 220 mM.

In certain embodiment the pH is selected from about 5.5, about 6.0, about 6.1, about 6.2, about 6.3, about 6.4, about 6.5, about 6.6, about 6.7, about 6.8, about 6.9, and about 7.0.

In an embodiment, the present invention provides an improved method for quantification and/or estimation of impurities in a protein sample comprising;

a) a protein mixture from harvest comprising CTLA4-IgG1 and size variant impurities;
b) loading the protein mixture to said Size exclusion High Performance Liquid Chromatography (SE-HPLC) Biosep SEC s2000 column;
c) separating the protein mixture with suitable mobile phase comprising combination of 100 mM Sodium phosphate in combination with 100 mM Sodium sulphate at pH 6.5;
d) analysed or quantified the pre-peak, post-peak and main peak of the protein mixture; wherein the SE-HPLC column provides the resolution of pre-peak is more than 1.3.

In an embodiment, the pre-peak impurity is high molecular weight and/or aggregates and post-peak impurity is low molecular weight and/or fragments of CTLA4-IgG1.

In an embodiment, the present invention provides an improved method for quantification and/or estimation of impurities in a protein sample comprising;

a) a protein mixture from harvest comprising CTLA4-IgG1 and size variant impurities;
b) loading the protein mixture to said Size exclusion High Performance Liquid Chromatography (SE-HPLC) Biosep SEC s2000 column;
c) separating the protein mixture with suitable mobile phase comprising combination of 100 mM Sodium phosphate in combination with 200 mM Sodium sulphate at pH 6.5;
d) analysed or quantified the pre-peak, post-peak and main peak of the protein mixture; wherein the SE-HPLC column provides the resolution of pre-peak is more than 1.3.

In an embodiment, the salt concentration used in mobile phase is selected from about 50 mM, about 60 mM, about 65 mM, about 70 mM, about 75 mM, about 80 mM, about 85 mM, about 90 mM, about 95 mM, about 100 mM, about 105 mM, about 110 mM, and about 115 mM, about 120 mM, about 125 mM, about 130 mM, about 135 mM, about 140 mM, about 145 mM, and about 150 mM of Sodium phosphate.

In another embodiment, the salt concentration used in mobile phase is selected from about 80 mM, about 90 mM, about 100 mM, about 110 mM, and about 120 mM of Sodium phosphate.

In preferred embodiment, the salt concentration used in mobile phase is about 100 mM of Sodium phosphate.

In an embodiment, the salt concentration used in mobile phase is selected from about 50 mM, about 60 mM, about 65 mM, about 70 mM, about 75 mM, about 80 mM, about 85 mM, about 90 mM, about 95 mM, about 100 mM, about 105 mM, about 110 mM, and about 115 mM, 120 mM, 125 mM, 130 mM, 135 mM, 140 mM, 145 mM and about 150 mM of Sodium sulphate.

In another embodiment, the salt concentration used in mobile phase is selected from about 80 mM, about 90 mM, about 100 mM, about 110 mM, and about 120 mM of Sodium sulphate.

In preferred embodiment, the salt concentration used in mobile phase is about 100 mM of Sodium sulphate.

In an embodiment, the salt concentration used in mobile phase is selected from about 100 mM, about 120 mM, about 130 mM, about 140 mM, about 150 mM, about 160 mM, about 170 mM, about 180 mM, about 190 mM, about 200 mM, about 210 mM, and about 220 mM of Sodium sulphate.

In another embodiment, the salt concentration used in mobile phase is selected from about 100 mM, about 150 mM, and about 200 mM of Sodium sulphate.

In preferred embodiment, the salt concentration used in mobile phase is about 200 mM of Sodium sulphate.

In an embodiment, the mobile phase is free of sodium chloride, arginine, acetonitrile, TFA, guanidine hydrochloride, urea and formic acid.

In an embodiment, the pH of mobile phase is adjusted to pH selected from about pH 5.5 to about pH 7.0, about pH 6.0 to about pH 7.0, about pH 6.5 to about pH 7.0, and about pH 6.7 to about pH 7.0.

In preferred embodiment, the pH of mobile phase is adjusted to about pH 6.5.

In an embodiment, the pH of mobile phase is adjusted by acid selected from sulphuric acid, hydrochloric acid (HCI), nitric acid and phosphoric acid.

In another embodiment, the pH of mobile is adjusted by acid selected from hydrochloric acid (HCI) and phosphoric acid.

In preferred embodiment, the pH of mobile is adjusted by Orthophosphoric acid.

In an embodiment, the flow rate of mobile phase is selected from about 0.1 mL/min, about 0.2 mL/min, about 0.3 mL/min, about 0.4 mL/min, about 0.5 mL/min, about 0.6 mL/min, about 0.7 mL/min, about 0.8 mL/min, about 0.9 mL/min and about 1.0 mL/min.

In another embodiment, the flow rate of mobile phase is selected from about 0.1 mL/min, about 0.2 mL/min, about 0.3 mL/min, about 0.4 mL/min, and about 0.5 mL/min.

In an embodiment, the flow rate of mobile phase is less than 0.6 mL/min.

In preferred embodiment, the flow rate of mobile phase is about 0.5±0.2 mL/min.

In an embodiment, the mobile phase is free of sodium chloride, arginine, acetonitrile, TFA, guanidine hydrochloride, urea and formic acid.

In an embodiment, the resolution of pre-peak is selected from about 1.3 to about 1.9.

In an embodiment, the resolution of pre-peak is from about 1.3, about 1.4, about 1.5, about 1.6, about 1.7, about 1.8, about 1.9.

In an embodiment, the resolution of pre-peak is 1.82.

The present invention provides an example for illustration purpose which should not be considered to limit the scope of the present invention with the described examples.

EXAMPLES

Process for estimation and/or quantification of pre-peak and main peak of protein mixture comprising CTLA4-IgG1 fusion protein.

Reagents Details:

a) Sodium phosphate dibasic anhydrous
b) Sodium phosphate monobasic monohydrate
c) Sodium sulphate anhydrous
d) Orthophosphoric acid
e) Sodium chloride
f) Potassium phosphate dibasic anhydrous
g) Potassium phosphate monobasic anhydrous
h) Potassium chloride
i) Milli Q water Equipment Details:

a) HPLC system equipped with a pump, an autosampler, a UV detector and a suitable data acquisition system
b) Digital Dry bath
c) Magnetic stirrer
d) pH meter
e) Analytical weighing balance
f) Sonicator
g) Filter assembly
h) 0.2 μm membrane filter

Example 1

Size exclusion chromatography Column selection: Column of different brands and dimensions were tried which could work for CTLA4-IgG1. Samples were diluted in mobile phase and injected to the column. Percentage (%) purity, USP Resolution and tailing was compared between different columns.

Sample (CTLA4-IgG1 fusion protein) was diluted from 25 mg/ml to 1 mg/ml in mobile phase. 30 μg sample was injected (injection volume 30 μl).

Chromatographic Conditions:

| | |
|---|---|
| HPLC system: | HPLC system equipped with a pump, an autosampler, a UV detector and a suitable data acquisition system |
| Columns: | Biosep SEC s2000 & TSKgel G3000swxl. |
| Mobile Phases: | Biosep SEC s2000:<br>100mM Sodium phoshphate + 100mM Na2SO4, pH 6.5<br>TSKgel G3000swxl: 100 mM potassium phosphate + 200 mM KCl, pH 6.5 |
| Mode: | Isocratic |
| Detection: | UV at 215nm |
| Flow Rate: | 0.5 ml/min |
| Injection Volume: | 30 μl |
| Injection Amount: | 30 μg |
| Column Temp.: | 30° C. |
| Sample Temp.: | 4-8° C. |
| Run time: | 60 minutes |
| Needle Wash: | 5% (v/v) Methanol in water |

The experiment is performed by incorporating injection/s of the blank solution followed by injection/s of reference protein standard onto mentioned chromatographic columns. Test sample which is CTLA4-IgG1 is injected onto the columns thereafter.

TABLE 1

Results for CTLA4-IgG reference in different columns

| Column | Total Pre-peak area percentage (%) | Total Post-peak area percentage (%) | Percentage (%) Purity | USP resolution of pre-peak | USP tailing |
|---|---|---|---|---|---|
| Biosep SEC s2000 | 0.94 | 0.53 | 98.52 | 1.82 | 1.12 |
| TSK gel G3000swxl | 1.29 | Not detected | 98.71 | 2.03 | 1.13 |

As shown in table 1, Biosep SEC s2000 has able to detect and quantify the post peak having 0.53% total area, where TSK gel G3000swxl fails to quantify post peak.

Example 2

Quantification of pre-peak, post-peak and main peak of protein mixture containing CTLA4-IgG1 fusion protein.

Sample (CTLA4-IgG1 fusion protein) was diluted from 25 mg/ml to 1 mg/ml in mobile phase, 30 μg sample was injected (injection volume 30 μl).
Chromatographic Conditions:

| | |
|---|---|
| HPLC system: | HPLC system equipped with a pump, an autosampler, a UV detector and a suitable data acquisition system |
| Column: | Biosep SEC s2000 |
| Mobile Phase: | Mobile phase (with column Biosep SEC s2000): 100 mM Sodium phosphate in combination with 100 mM $Na_2SO_4$, pH 6.5 |
| Mode: | Isocratic |
| Detection: | UV at 215 nm |
| Flow Rate: | 0.5 ml/min |
| Injection Volume: | 30 μl |
| Injection Amount: | 30 μg |
| Column Temp.: | 30° C. |
| Sample Temp.: | 4-8° C. |
| Run time: | 60 minutes |
| Needle Wash: | 5% (v/v) Methanol in water |

The experiment is performed by incorporating injection/s of the blank solution followed by injection/s of reference protein standard onto chromatographic column Biosep SEC s2000. Test sample which is CTLA4-IgG1 fusion protein is injected onto Biosep SEC s2000 column thereafter.

TABLE 2

Results for Percentage (%) purity or Main peak area percentage (%), pre-peak area percentage (%) and post-peak area percentage (%) in Biosep SEC s2000 column:

| Column | Total Pre-peak area percentage (%) | Percentage (%) Purity | Total Post-peak area percentage (%) | USP resolution of pre-peak | USP tailing |
|---|---|---|---|---|---|
| Biosep SEC s2000 | 0.94 | 98.52 | 0.53 | 1.82 | 1.12 |

As shown in Table 2, Biosep SEC s2000 column provides 98.52% purity and 0.94% of total pre-peak area and 0.53% of total post-peak area and 1.82 pre-peak resolution of CTLA4-IgG1 fusion protein.

Example 3

Comparison of mobile phase for quantification of pre-peak, post-peak and main peak of protein mixture containing CTLA4-IgG1 fusion protein.

For SE HPLC, mobile phase with either sodium or potassium salt can be used. Sodium or potassium salts with different salt concentration were used with Biosep SEC column. Resolution of impurities was compared between different mobile phases.

Sample (CTLA4-IgG1 fusion protein) was diluted from 25 mg/ml to 1 mg/ml in mobile phase. 30 μg sample was injected (injection volume 30 μl).
Chromatographic Conditions:

| | |
|---|---|
| HPLC system: | HPLC system equipped with a pump, an autosampler, a UV detector and a suitable data acquisition system |
| Column: | Biosep SEC s2000 |
| Mobile Phase: | Mobile phase (with column Biosep SEC s2000):<br>a) 100 mM Sodium phosphate in combination with 100 mM Na2SO4, pH 6.5<br>b) 100 mM Sodium phosphate in combination with 200 mM Na2SO4, pH 6.5<br>c) 100 mM Sodium phosphate in combination with 100 mM NaCl, pH 6.5<br>d) 100 mM Sodium phosphate in combination with 200 mM NaCl, pH 6.5<br>e) 100 mM Potassium phosphate in combination with 200 mM KCl, pH 6.5 |
| Mode: | Isocratic |
| Detection: | UV at 215 nm |
| Flow Rate: | 0.5 ml/min |
| Injection Volume: | 30 μl |
| Injection Amount: | 30 μg |
| Column Temp .: | 30° C. |
| Sample Temp .: | 4-8° C. |
| Run time: | 60 minutes |
| Needle Wash: | 5% (v/v) Methanol in water |

In present example, all the column conditions were kept constant except the mobile phase. Applicant has tried both the above-mentioned mobile phase a) to e) to observe the effect of mobile phase over the quantification of pre-peak, post-peak and main peak of protein mixture containing CTLA4-IgG1 fusion protein.

Figure 3:
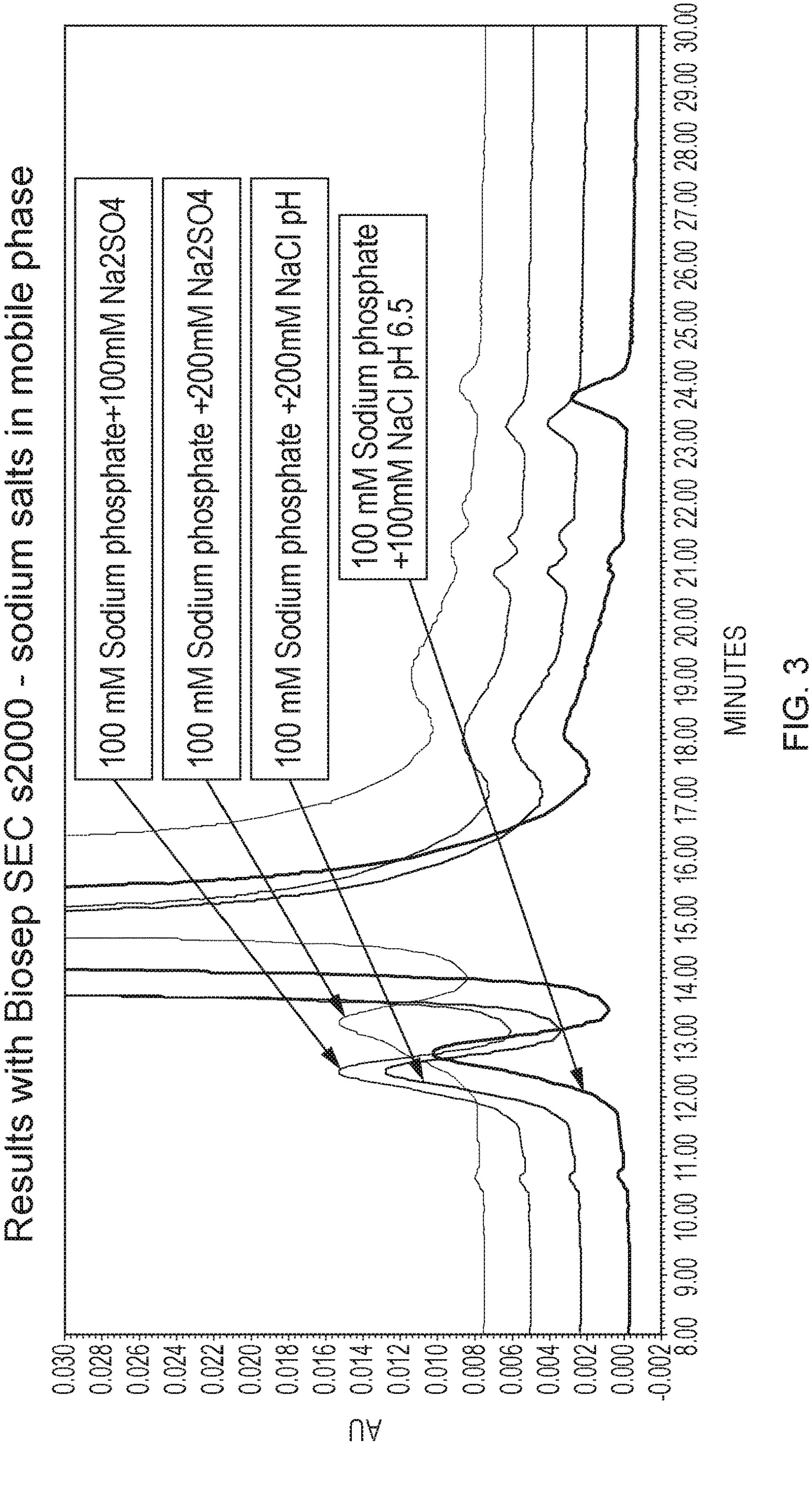
FIG. 3 shows the comparative effect of mobile phase having 100 mM Sodium phosphate with 100 mM $Na_2SO_4$, 100 mM and 200 mM NaCl, pH 6.5.
Figure 4:
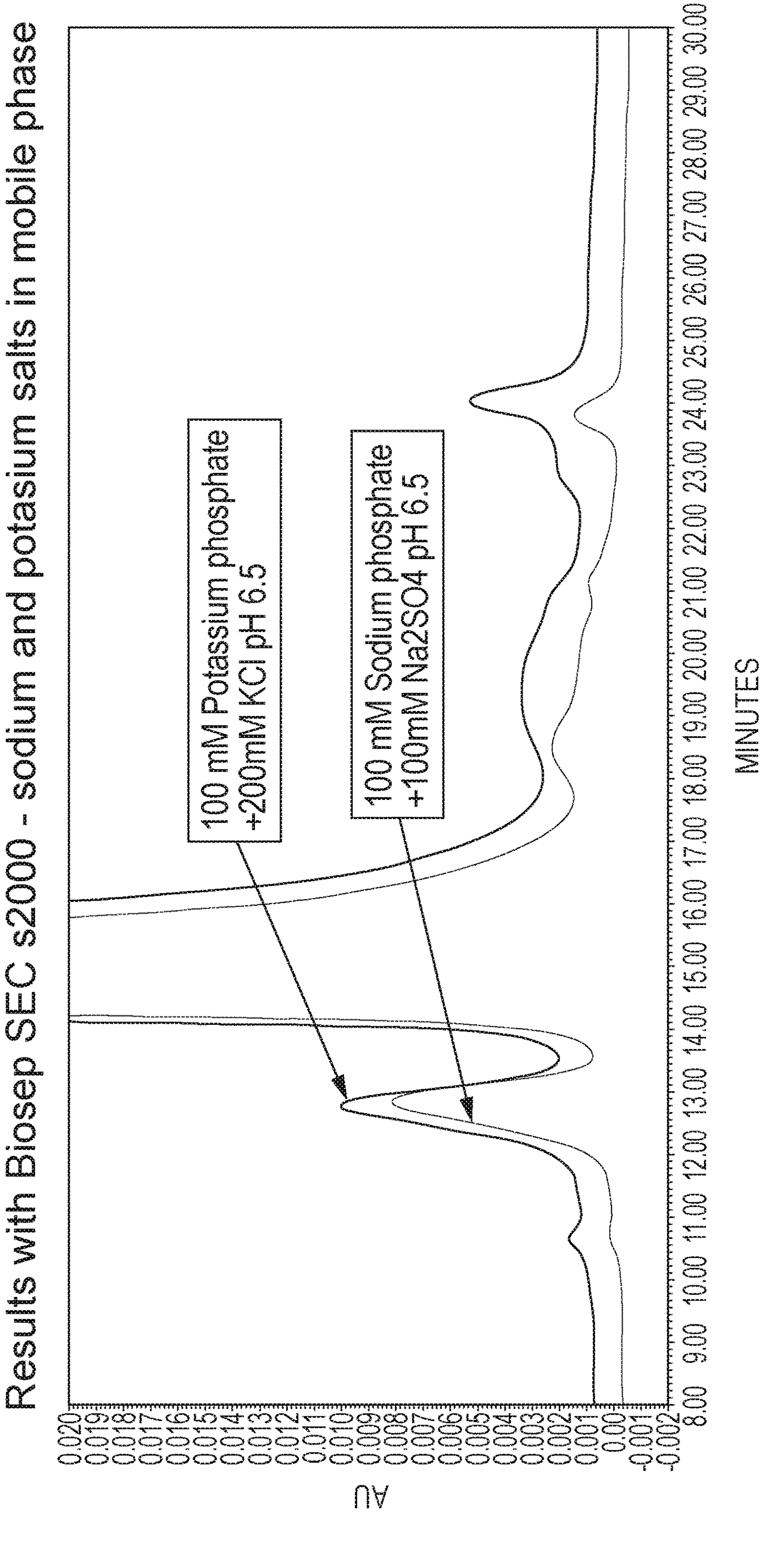
FIG. 4 shows the comparative effect of mobile phase having 100 mM Sodium phosphate with 100 mM $Na_2SO_4$ compared with mobile phase having Potassium phosphate with 200 mM KCl, pH 6.5.

In Biosep SEC s2000 column, Sodium phosphate with 100 mM Na2SO4, 100 mM and 200 mM NaCl gave comparable profile as shown in FIG. 3. Pre-peak broadening was observed with 200 mM Na2SO4. When mobile phase with potassium salt was used with Biosep column, post peak impurity becomes broad (peak shape is distorted) as seen in FIG. 4.

Hence with Biosep SEC s2000 column mobile phase with sodium salts that is 100 mM Sodium phosphate in combination with 100 mM Na2SO4, pH 6.5 showed adequate pre-peak area or area percentage (%) and post peak area or area percentage (%), good purity and sharp resolution of pre-peak, post peak and main peak of protein mixture containing CTLA4-IgG1 fusion protein.

Example 4

Flow rate optimization study for quantification of pre-peak and main peak of protein mixture containing CTLA4-IgG1 fusion protein:

Two different flow rates 0.5 ml/min and 0.3 ml/min were tried for SE HPLC with TSK gel G3000swxl column.

Experimental details for flow rate optimization:

| Sample preparation details | Chromatographic conditions | Processing method |
|---|---|---|
| Reference Sample (CTLA4-IgG1) was diluted from 25 mg/ml to 1 mg/ml in mobile phase.<br>30 μg sample was injected (injection volume 30 μl). | Column: TSKgel G3000swxl Column<br>Temperature: 30° C.<br>Mode: Isocratic<br>Run time: 60 min<br>Detection wavelength: 215 nm<br>Mobile phase: 100 mM Potassium phoshphate + 200 mM KCl, pH 6.5<br>Flow rate 1: 0.5 ml/min<br>Flow rate 2: 0.3 ml/min | 0.5 ml/min flow rate<br>Integration Algorithm: Apex<br>Track Start time: 10.5 min<br>End time: 21 min Peak width (sec): 50<br>Detection threshold: 7.000e+01<br>Suitability parameter: On<br>0.3 ml/min flow rate<br>Integration Algorithm: Apex<br>Track Start time: 17 min<br>End time: 35 min<br>Peak width (sec): 50<br>Detection threshold: 8.000e+01<br>Suitability parameter: On |

TABLE 3

| Comparative data for different flow rate: | | | | | |
|---|---|---|---|---|---|
| Flow rate (ml/min) | Total Pre-peak area percentage (%) | Total Post peak area percentage (%) | Percentage (%) purity | Pre-peak resolution | USP tailing |
| 0.5 | 1.29 | Not detected | 98.71 | 2.03 | 1.13 |
| 0.3 | 1.05 | Not detected | 98.94 | 2.04 | 1.10 |

Figure 5:
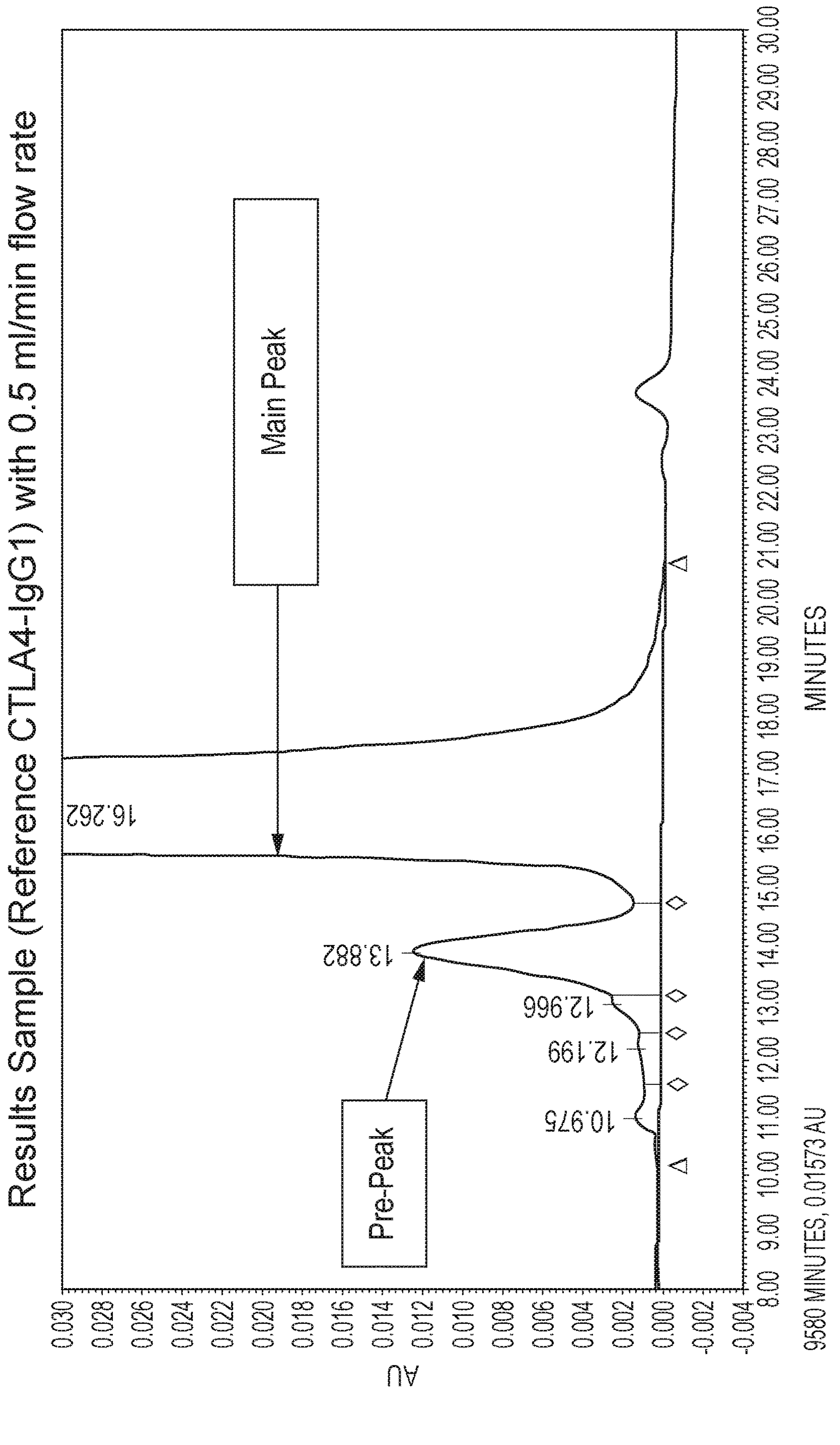
FIG. 5 shows the results Sample (Reference CTLA4-IgG1) with 0.5 ml/min flow rate.
Figure 6:
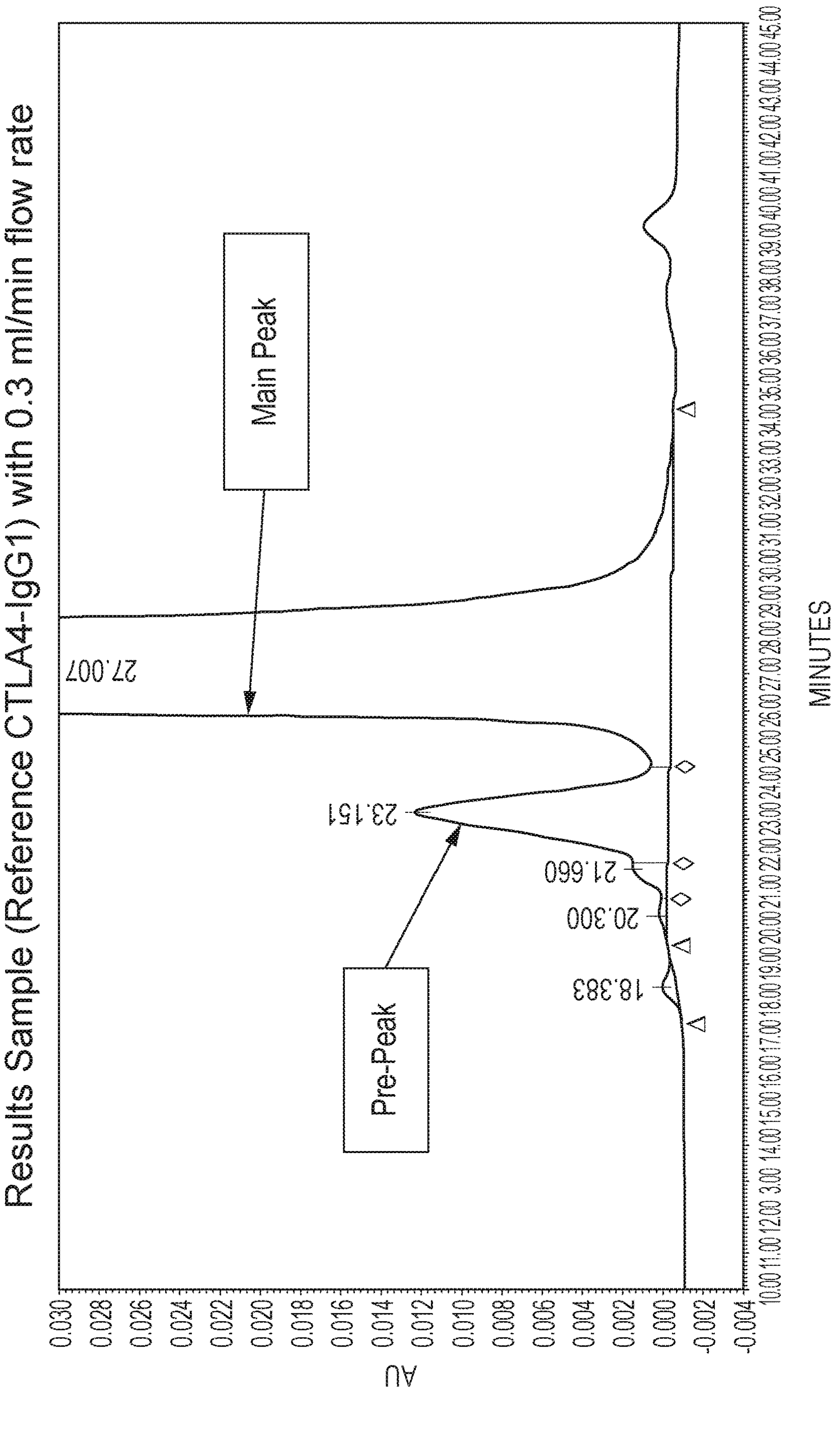
FIG. 6 shows the results Sample (Reference CTLA4-IgG1) with 0.3 ml/min flow rate.

Above table 3 data shows, total pre-peak area percentage (%) was slightly lower with 0.3 ml/min flow rate as compared to 0.5 ml/min. Hence 0.5 ml/min flow rate was finalized. Refer FIGS. 5 & 6. However. TSKGel is failed to detect postpeak in CTLA4-IgG1 column.

We claim:

1. An improved method for the separation of CTLA4-IgG1 fusion protein mixture comprising CTLA4-IgG1 fusion protein, pre-peak impurity thereof and post-peak impurity thereof, the process comprising:

a) loading the CTLA4-IgG1 fusion protein mixture onto Size Exclusion High Performance Liquid Chromatography (SE-HPLC) column;

b) separating the CTLA4-IgG1 fusion protein, the pre peak impurity and the post peak impurity present in the CTLA4-IgG1 fusion protein mixture through SEC-HPLC column with a mobile phase comprising a combination of salts, at a suitable pH, wherein the suitable pH is more than pI of the CTLA4-IgG1 fusion protein, and wherein the mobile phase maintains a flow rate of about 0.5 ml/min; and c) separating the pre-peak impurity and the post-peak impurity from the CTLA4-IgG1 fusion protein; wherein the pre-peak impurity resolution is more than 1.3, wherein the area of the pre-peak impurity and the post-peak impurity is not merged or interfered with the area of the CTLA4-IgG1 fusion protein, wherein the CTLA4-IgG1 fusion protein is abatacept; and wherein the mobile phase has a pH of about 6.5 to about 6.7.

2. The method according to claim 1, wherein the pre-peak impurity, the post peak impurity and the CTLA4-IgG1 fusion protein is further quantified at suitable detection absorbance selected from about 214 nm to about 280 nm.

3. The method according to claim 1, wherein the CTLA4-IgG1 fusion protein mixture is obtained from harvest or any other purification methods.

4. The method according to claim 1, wherein the protein mixture is obtained from affinity chromatography.

5. The method according to claim 1, wherein the pre-peak impurity is high molecular weight and/or aggregates and the post-peak impurity is low molecular weight and/or fragments of CTLA4-IgG1.

6. The method according to claim 1, wherein the combination of salts of the mobile phase is selected from sodium phosphate in combination with sodium sulphate, potassium phosphate in combination with potassium chloride, sodium phosphate in combination with potassium chloride, and potassium phosphate in combination with sodium sulphate in suitable concentration selected from about 50 mM to about 150 mM.

7. The method according to claim 6, wherein the combination of salts of the mobile phase is sodium phosphate in combination with sodium sulphate in suitable concentration selected from about 80 mM to about 120 mM.

8. The method according to claim 1, wherein the mobile phase is free of sodium chloride, arginine, acetonitrile, TFA, guanidine hydrochloride, urea and formic acid.

9. The method according to claim 1, wherein the loading of the CTLA4-IgG1 fusion protein mixture comprises about 30 μg/μl to about 80 μg/μl.

10. The method according to claim 1, wherein the SE-HPLC column has silica matrix, pore size of the SE-HPLC column is about 140 Å to about 290 Å and dimension of the SE-HPLC column is selected from 150*4.6 mm and 300*7.8 mm.

11. The method according to claim 10, wherein pore size of the SE-HPLC column is about 145 Å to about 200 Å and dimension of the SE-HPLC column is 300*7.8 mm.

12. The method according to claim 10, wherein the SE-HPLC column is BioSep-SEC-S2000, BioSep-SEC-S3000, or BioSep-SEC-S4000.

13. The method according to claim 1, wherein the peak tailing is from about 0.7 to 1.15.

14. The method according to claim 1, wherein the pI of the CTLA4-IgG1 fusion protein is less than 6.5.

15. The method according to claim 1, wherein the purity of the CTLA4-IgG1 fusion protein is more than 98%.

16. An improved method for the separation of CTLA4-IgG1 fusion protein mixture comprising CTLA4-IgG1 fusion protein, pre-peak impurity thereof and post-peak impurity thereof, the process comprising:

a) loading the CTLA4-IgG1 fusion protein mixture onto Size Exclusion High Performance Liquid Chromatography (SE-HPLC) column;

b) separating the CTLA4-IgG1 fusion protein, the pre peak impurity and the post peak impurity present in the CTLA4-IgG1 fusion protein mixture through SEC-HPLC column with a mobile phase comprising a combination of salts, at a suitable pH, wherein the suitable pH is more than pI of the CTLA4-IgG1 fusion protein, and wherein the mobile phase maintains a flow rate of about 0.4 ml/min; and c) separating the pre-peak impurity and the post-peak impurity from the CTLA4-IgG1 fusion protein; wherein the pre-peak impurity resolution is more than 1.3, wherein the area of the pre-peak impurity and the post-peak impurity is not merged or interfered with the area of the CTLA4-IgG1 fusion protein, wherein the CTLA4-IgG1 fusion protein is abatacept; and wherein the mobile phase has a pH of about 6.5 to about 6.7.

17. An improved method for the separation of CTLA4-IgG1 fusion protein mixture comprising CTLA4-IgG1 fusion protein, pre-peak impurity thereof and post-peak impurity thereof, the process comprising:

a) loading the CTLA4-IgG1 fusion protein mixture onto Size Exclusion High Performance Liquid Chromatography (SE-HPLC) column;

b) separating the CTLA4-IgG1 fusion protein, the pre peak impurity and the post peak impurity present in the CTLA4-IgG1 fusion protein mixture through SEC-HPLC column with a mobile phase comprising a combination of salts, at a suitable pH, wherein the suitable pH is more than pI of the CTLA4-IgG1 fusion protein, and wherein the mobile phase maintains a flow rate of about 0.6 ml/min; and c) separating the pre-peak impurity and the post-peak impurity from the CTLA4-IgG1 fusion protein; wherein the pre-peak impurity resolution is more than 1.3, wherein the area of the pre-peak impurity and the post-peak impurity is not merged or interfered with the area of the CTLA4-IgG1 fusion protein, wherein the CTLA4-IgG1 fusion protein is abatacept; and wherein the mobile phase has a pH of about 6.5 to about 6.7.

* * * * *